United States Patent [19]

Sherman

[11] Patent Number: 4,891,218
[45] Date of Patent: Jan. 2, 1990

[54] RODENTICIDE BAIT BLOCK

[76] Inventor: Daniel A. Sherman, 1355 Bobolink Pl., Los Angeles, Calif. 90069

[21] Appl. No.: 841,426

[22] Filed: Dec. 15, 1986

Related U.S. Application Data

[63] Continuation of Ser. No. 761,904, Aug. 2, 1985, abandoned.

[51] Int. Cl.$^4$ .............................................. A01N 25/00
[52] U.S. Cl. ........................................ 424/84; 424/410
[58] Field of Search ................. 424/15, 17, 84; 43/58; 424/410

[56] References Cited

U.S. PATENT DOCUMENTS

| | | | |
|---|---|---|---|
| D. 89,941 | 5/1933 | Low | 424/15 |
| D. 98,858 | 3/1936 | Gager | 424/15 |
| 982,711 | 1/1911 | Ellis | 426/805 |
| 1,156,584 | 10/1915 | Bloom | 424/2 |
| 1,174,695 | 3/1916 | Dawson | 424/2 |
| 1,220,593 | 3/1917 | Berg | 424/17 |
| 1,695,567 | 12/1928 | Weber | 426/805 |
| 1,915,392 | 6/1933 | Thomson | 426/660 |
| 2,132,690 | 10/1938 | Hilliand | 424/15 |
| 2,813,058 | 11/1957 | Smith | 424/17 |
| 3,071,476 | 1/1963 | Werft et al. | 424/15 |
| 3,105,321 | 10/1963 | Link | 424/17 |
| 3,113,076 | 12/1963 | Jacobs | 424/15 |
| 3,816,610 | 1/1972 | Lusby | 424/17 |
| 4,376,111 | 3/1983 | Tovey | 424/15 |

FOREIGN PATENT DOCUMENTS

| | | |
|---|---|---|
| 717369 | 1/1932 | France. |
| 1130497 | 11/1955 | France. |
| 352208 | 9/1937 | Italy. |
| 58-013503 | 1/1983 | Japan. |
| 189400 | 11/1922 | United Kingdom. |

OTHER PUBLICATIONS

Kosikowski, "Cheese and Fermented Milk Foods", Published by The Author, Cornell University, 1966, Chapter 13, pp. 224–241, Chapter 11, pp. 182–193.
Advertisement, Chempar, p. 25, Pest Control, Nov. 1985.

*Primary Examiner*—Morton Foelak
*Assistant Examiner*—Nathan M. Nutter

[57] ABSTRACT

This invention relates to parafinized rodenticide bait blocks in general and, more specifically to the actual form of these bait blocks.

The invention concerns itself with the physical construction and shape of the block and will provide a more effective rodenticide by providing a bait block that will have a continuous biting surface that a rodent such as a mouse or rat can knaw at at all times as the block is being consumed.

The use of this block provides the user with an individual and metered portion of bait designed to be more effective in eliminating household rodents such as Norway Rats, Roof Rats and House Mice and will, by its use, insure the total consumption of the bait block, thereby providing increased efficacy of the block and greater safety in the use of these poisoned blocks because less residual bait is left behind.

2 Claims, 1 Drawing Sheet

RODENTICIDE BAIT BLOCK

This application is a continuation-in-part of application Ser. No. 761,904, filed Aug. 2, 1985, and now abandoned.

BACKGROUND OF THE INVENTION

Rodents have plagued mankind for centuries by competing for food, spreading disease and by destroying the character of neighborhoods.

They have been known to attack humans, they foul foodstuffs with their droppings, dirt and parasites.

Over the year there have been many solutions proposed to eliminate rodent populations but, the most effective and widespread method of eliminating a rodent population has been to kill them with poisoned baits.

Baits have taken the form of impregnated grains and foods, formed into small pellets and poisons have been placed in various sizes of parafinized blocks.

Each of these forms have had inherent individual drawbacks such as the tendency of rodents to scatter impregnated grains and pellets and the reluctance or rodents, especially mice, to consume larger forms of bait blocks.

Additionally, the aforementioned methods of fabricating are defective for the following reasons; rodents, in spreading bait as they ate presented a significant potential for the poisoning of non target species and, even when bait was placed in tamper-resistant bait stations, there was a tendency for the bait to scatter as the rodents passed through the stations, or, if the stations were upset by activity in the environment.

When larger blocks of bait were fabricated out of material such as parafinized materials, the rodents, who have a tendency to nibble at their food sources would select more palitable alternative foods in the surrounding areas thereby defeating the control program.

House mice, who are particularly selective in their feeding habits, would ignore the larger bait blocks because they shyed away from baits offered in the forms that only provided flat surfaces that precluded their natural method of food consumption by knawing at the rough edges or small exposed surfaces of foods.

With the introduction of advanced and more powerful rodenticide products that were designed to destroy rodents in a single feeding, a method of presenting baits to target rodents such as Norway Rats, Roof Rats or House Mice in individual and metered portions that were more secure and stable became necessary.

In order to provide this, a method of providing a parafinized bait block that would afford a continous irregular surface for the rodent to knaw at and that would prvide a contious biting edge in order to make the bait more palatable, became an absolute necessity.

The object of the instant invention is to improve the state of the art in the presentation of baits to target rodents and to provide a structure of bait, in individually sized blocks, that will allow the rodent to consume the bait and, while consuming the bait, will cause the remaining portion of the bait block top have an irregular form and a biting edge that the rodents can knaw on.

Still another object of the instant invention is to provide a stable rodenticide that can be placed in a container or secured to a floor peg and, that will inhibit movement of the bait as it is consumed.

A further object of the invention is to provide a replicable and uniform individual bait block portion, constructed of parafinized material, that will be accepted by target rodents more readily.

Still another object of the invention is to conserve the amount of bait consumed by an individual rodent who, after injesting a rodenticide that requires multiple feedings, would normally remove and hide ramaining bait, even after consuming a lethal dose.

These, and other objects, advantages and novel features of the invention will become apparent from the following description of the invention when considered in conjunction with the accompanying drawings.

Reference is made to the following prior patents both U.S. and foreign 3105321 Link 10/63, Class 424, 1220593 Berg 3/17, Class 424, 1174695 Dawson 3/16, Class 424, 1156584 Bloom 10/15, Class 424, 2813058 Smith 11/57, Class 424, 3816610 Lusby 6/74, Class 424, 1915392 Rhomson 6/33, Class 426, 2132690 Hilliard 10/38, Class 424, 982711 Ellis 1/11 Class 426, 1695567 Weber 12/28, Class 426, D098858 Gager 3/36, Class D1, D89941 Low 5/33, Class 424, 3071496 Jacobs 12/63, Class 424, 376111 Tovey 3/83, Class 424—Foreign 717369 France, Mauler 10/31, Class 424, 0164102 Japan 12/81 Matswhita, Class 424, 0013503 Japan, Kyowasangio 1/83, Class 424, D068083 France, Renaud 1/83, Class 424 189400 Great Britain, Walton 11/22, Class 424352208 Italy Soc. A. Perigina 9/37, Class 424, 21156976 Great Britan, Walton 9/83, Calss 424, 2115698A, Great Britian Gschwind, Calss 424, 1233115 France, S.A.R.L. 10/60, Calss 424, 0120501 Japan Nitto Elec 9/80, Class 4240164101 Japan Matsushita 12/81, Calss 4240046901 Japan Matsuhita 3/81, Class 424.

The above cited patents are defective in that they are not readily replicable, depend on the addition of pisoned material to standard and available foodstuffs that do not maintain a regular and predicable pattern of continous knawing surfaces as they are consumed and do not take into account the effect of diverse toxins on differing species of household rodents, Additionally, the cited patents do not maintain a relationship between a predetermined patern of exterior protuberances and grooves and an internal structure of holes.

Further, the exterior pattern that appear on extruded or molded forms of food product as cited in the patents are designed to give the products extra strength in shipping and handling and are not claimed to provide a continous biting edge that appears as a rodent consumes the product or bait. Additionally, many of the cited patents contain flangible grooves used to break a larger portion of the product into smaller pieces. This is not in fact a feature of the present invention and the concept of flangible grooves to divide a larger unit to smaller pieces is not claimed in the instant invention.

DETAILED DESCRIPTION OF THE PREFERRED EMBODIMENT

Figure 1:
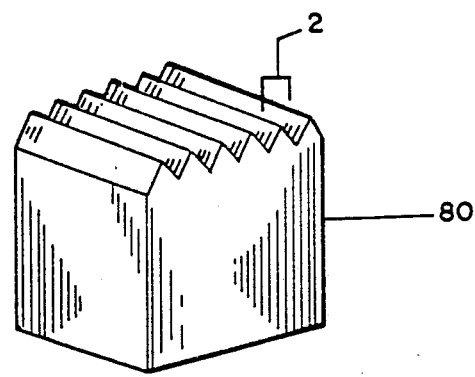
FIG. 1 show the bait block in total perspective and demonstrates the use of a geometically shaped surface that provides the initial biting edge that the rodent will bite at, chipping off smaller bite size portions.

As can be seen in FIG. 1, the bait block is formed generally as 80 and proportioned so that each block represents enough concentrated active rodenticide to kill an average colony of rats or mice.

The top of the block is formed with a series of hills and valleys spaced approximately ¼ inch between the top of each peak and the bottom of each valley.

These grooves running along the top surface of the bait block from front to back or from side to side represent the primary biting surface that is designed to allow the target rodent an edge to grab with its teeth and to break off into a convientient size for him to consume.

Additionally, the block is contructed of a parafinized material that will allow it to hold its shape while being consumed and the block will also be impregnated with an active rodenticide such as warfarin, bromodiolone, brodifacoum, or such active rodent killing material as may be needed to eliminate the population.

It should be noted that the grooves formed on the surface or sides of said bait blocks are exclusive of flagable grooves used for breaking larger blocks into smaller portions.

The actual size of the individual bait block would be based upon the $LD^{50}$ of the actove rodenticide in order to provide a minimum concentration of poisoned material in a single area.

Figure 2:
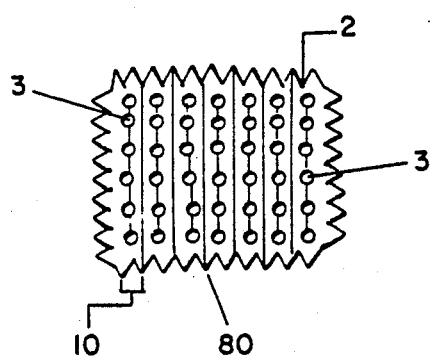
FIG. 2 is a top perspective of the bait block that demonstrates along with the geometrically shaped top surface, a series of holes that have been formed in the block and that will provide a continuous irregular surface, that will be presented to the rodent, as it consumes portions of the bait block. Also demonstrated is the use of geometrically shaped sides that provide additional biting edges for the rodent to bite at when attacking the block from the side.

Reference is also made to FIG. 2 which demonstrates that as part of the construction of the block 80 the sides of the block may also include the ridges and protuberances indicated above as 2 with regular dimensions between their peaks as indicated as 10.

FIG. 2 also demonstrates the use of holes 3 that have been drilled or formed through the block. The holes would be approximately ¼ inch in size and in relation to the size of the distances between the peaks and valley of the top of side protuberances would be relatively the same.

The purpose of said relativity is to establish a pattern of grooves that would remain contant as the rodent consumed the bait block with biting edges appearing as it ate into the block.

Based upon the toxisity of currently available rodenticides it would be estimated that each individual block would be approximately 1 inch high by 1½ wide and deep. These dimensions would vary depending on the target species or rodent, ie: Norway rat, roof rat, house mouse, etc. and what a lethal dose of rodenticide would be needed to kill the population.

Because the block is in an individual size that is small enough to easily hide in out of the way places that rodents travel in, more then on block might be used in areas of high rodent population or were the rodenticide used required multiple feedings.

Figure 4:
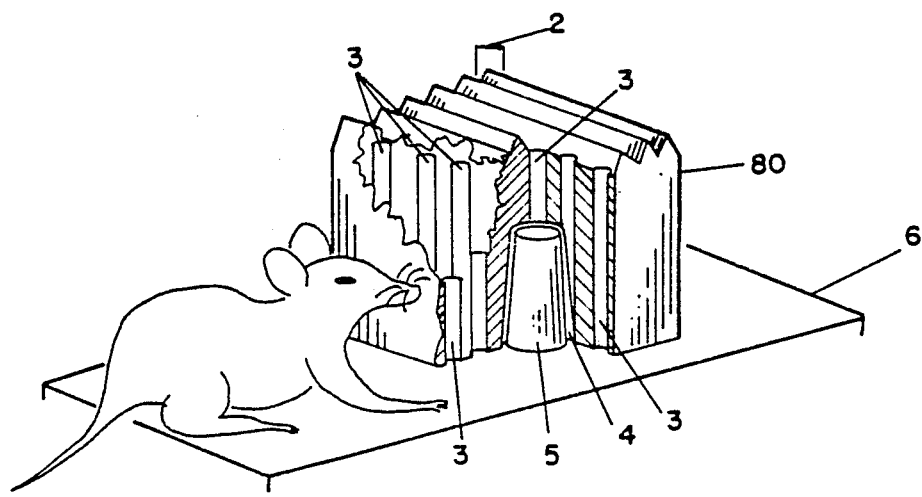
FIG. 4 shows a perspective of the block as the rodent is consuming the bait and depicts how the ridges and exposed holes formed through the block causes the exposed surfaces to be ireegular and roughly geometrical, thereby presenting a rough continuous biting edge that the rodent can knaw at, chipping away smaller pieces and exposing additional biting surfaces.

In FIG. 4 we see the establishment of the relationships between exterior protuberances 2 in block 80 and the internal holes 3 that have been formed in the blocks structure.

The rodent depicted in the block has gnawed away at the exterior wall leaving the same relationship of peaks and valleys that appeared on the exterior surface of block 80 on the now exposed surfaces of the interior of the block.

Figure 3:
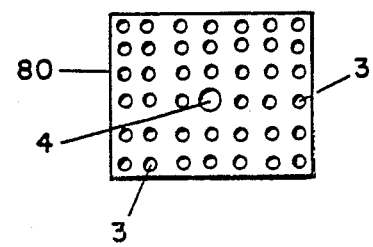
FIG. 3 depicts the bottom of the bait block showing the holes formed in the block and continuing through the bait block to the bottom. Also depicted is a larger center hole that is used to hold the bait block in place when placed on a peg mounted to a flat surface and to prevent the block from being moved or pulled away by the rodent.

Additionally, we note that in FIG. 3 a larger center hole 4 has been formed in the block to allow the block to be mounted to a peg and stabilized as the target rodent gnaws at it.

When this hole 4 is used in conjunction with the baiting program established with the use of these individual block, it prevents the rodent from carrying the block off and possibly exposing it to a non-target species.

It should be noted that the relationship between the shapes of the block are generally simetrical and deliberately manufactured to produce a specific desired result as the block is consumed, that of providing a biting edge that makes the block more attractive to a gnawing rodent then competing food sources.

This is significantly different then those holes formed in food products such as Swiss Cheese or formed by the use of adding a food additive to the block that may, such as nuts, form random edges that can be either gnawed flat or may disapear as the rodent consumes the food source.

Also considered in the formation of the patern of holes, protuberances and grooves is the size ranges of the target rodent species, its teeth charicteristics and its natural feeding paterns.

These holes, protuberances and grooves are formed and placed in such a manner as to insure the maximum kill per bait block and to avoid a rodent populations characteristic competition for food sources.

Now, more then one rodent can feed at the same block with all sharing equally palitable surfaces as they consume the rodenticide.

A target such as a house mouse will normally consume 2 grams of food per day. With the use of these controlled portions the mouse will consume his 2 grams and leave behind uncomsumed rodenticide for other members of his colony. This overcomes the tendency of rodents to "squirrel" away pelletized baits that will never be eaten and may in fact be placed in areas that represent a danger to other non-target species.

This metering of the amount of bait by the use of a relationship of geometrical shapes will also effect a substantial savings in the use of poisoned baits for rodent control due to the fact that the amount of time needed to kill the rodent may vary from species to species and from size to size as well as from active rodenticide to active rodenticides.

What I claim is:

1. A rodenticide bait block containing an active rodenticide capable of killing a target rodent such as a rat or mouse; said block having on one or more of its exterior surfaces a series of protuberances and grooves; said protuberances and grooves cooperating with each other to form geometrical ridges as a primary biting edge that rodent can attack and gnaw off in consuming said block; said block having running through its body a series of vertical holes that are relative to the exterior protuberances and grooves so as to produce continuous irregular rough biting edges as said block is consumed by the rodent and the exterior protuberances and grooves are eaten away.

2. A rodenticide bait block as in claim 1 whose dimension and body weight is determined as a metered amount of poison needed to kill a specifically numerical number of rodents that would appear in an average size colony of target rodents.

* * * * *